United States Patent [19]
Plevy et al.

[11] Patent Number: 5,968,741
[45] Date of Patent: Oct. 19, 1999

[54] METHODS OF DIAGNOSING A MEDICALLY RESISTANT CLINICAL SUBTYPE OF ULCERATIVE COLITIS

[75] Inventors: Scott E. Plevy, Tenafly, N.J.; Stephan R. Targan, Santa Monica, Calif.

[73] Assignee: Cedars-Sinai Medical Center, Los Angeles, Calif.

[21] Appl. No.: 08/837,302

[22] Filed: Apr. 11, 1997

[51] Int. Cl.$^6$ .......................... C12Q 1/68; G01N 33/569
[52] U.S. Cl. ................................ 435/6; 435/7.31
[58] Field of Search ....................... 435/7.31, 6

[56] References Cited

FOREIGN PATENT DOCUMENTS

WO 95/31575  11/1995  WIPO .

OTHER PUBLICATIONS

Barnes et al., "SErum antibodies reactive with *Saccharomyces cerevisiae* in inflammatory bowel disease: is IgA antibody a marker for Crohn's disease?", Int. Arch. Allergy Appl. Immunol; 92:9–15, 1990.

Colombel et al., Evidence for a specific antibody response to *Saccharomyces cerevisiae* oligomannosidic epitopes in Crohn's disese. Gastroenterology; 108:A800, Apr. 1995.

Colombel et al., "Anti–*Saccharomyces cerevisiae* antibodies: a new subclinical marker for Crohn's disease", Gastroenterology; 110:A886, May 1996.

Plevy et al.,"Tumor necrosis factor microsatelites define a Crohn's disease–associated haplotype on chromosome 6", Gastroenterology; 110:1053–1060, 1996.

Wiedbrauk et al., "Introduction to molecular methods for virus detection", Diagnostic Molecular Virology Workshop, Pan American group for Rapid Viral Diagnosis, Clearwater Beach, Florida, Apr. 1995.

Faille et al., "Evaluation of an Enzyme Immunoassay Using Neoglycolipids Constructed from *Candida albicans* Oligomannosides to Define the Specificity of Anti–Mannan Antibodies," *Eur. J. Clin. Microbiol. Infect. Dis.* 11:438–446 (1992).

Giaffer et al., "Antibodies to *Saccharomyces cerevisiae* in Patients With Crohn's Disease and Their Possible Pathogenic Importance," *Gut* 33:1071–1075 (1992).

Hanauer, "Inflammatory Bowel Disease," *New Engl. J. Med.* 334:841–848 (1996).

(List continued on next page.)

*Primary Examiner*—Donna C. Wortman
*Assistant Examiner*—Brenda G. Brumback
*Attorney, Agent, or Firm*—Campbell & Flores LLP

[57] ABSTRACT

The present invention provides serological and genetic methods of diagnosing a medically resistant clinical subtype of ulcerative colitis UC. The present invention provides a method of diagnosing a medically resistant clinical subtype of UC by determining the presence or absence of anti-*Saccharomyces cerevisiae* antibodies (ASCA) in a patient with UC, where the presence of ASCA indicates the medically resistant clinical subtype of UC. The present invention also provides a method of diagnosing a medically resistant clinical subtype of UC by determining the presence or absence of a TNFa2b1c2d4e1 haplotype in a patient with UC, where the presence of said TNFa2b1c2d4e1 haplotype indicates the medically resistant clinical subtype of UC. In addition, the invention provides a method of diagnosing a medically resistant clinical subtype of UC by determining the presence or absence of a TNFa2b1c2d4e1 haplotype in a patient with UC and determining the presence or absence of ASCA in the patient with UC, where the presence of said TNFa2b1c2d4e1 haplotype indicates the medically resistant clinical subtype of UC and the presence of ASCA independently indicates the medically resistant clinical subtype of UC. The invention further provides kits for diagnosing a medically resistant clinical subtype of UC containing antigen specific for ASCA and one or more oligonucleotide primers complementary to a nucleotide sequence flanking TNF microsatellite locus TNFa, TNFb, TNFc, TNFd or TNFe.

46 Claims, 1 Drawing Sheet

OTHER PUBLICATIONS

Hanauer and D'Haens, "Medical Management of Ulcerative Colitis," in Targan and Shanahan, *Inflammatory Bowel Disease: From Bench to Bedside* Williams and Wilkens, pp. 545–561 (1994).

Jongeneel et al., "Extensive Genetic Polymorphism in the Human Tumor Necrosis Factor Region and Relation to Extended HLA Haplotypes," *Proc. Natl. Acad. Sci. USA* 88:9717–9721 (1991).

Lindberg et al., "Antibody (IgG, IgA, and IgM) to Baker's Yeast (*Saccharomyces cerevisiae*), Yeast Mannan, Gliadin, Ovalbumin and Betalactoglobulin in Monozygotic Twins with Inflammatory Bowel Disease," *Gut* 33:909–913 (1992).

Main et al., "Antibody to *Saccharomyces cerevisiae* (baker's yeast) in Crohn's Disease," *British Medical Journal* 297:1105–1106 (1988).

McKenzie et al., "Antibody to Selected Strains of *Saccharomyces cerevisiae* (baker's and brewer's yeast) and *Candida albicans* in Crohn's Disease," *Gut* 31:536–538 (1990).

McKenzie et al., "Antigenic Heterogeneity of Strains of *Saccharomyces cerevisiae* and *Candida albicans* Recognized by Serum Antibodies from Patients with Crohn's Disease," *FEMS Microbiology Immunology* 89:219–224 (1992).

Nedospasov et al., "DNA Sequence Polymorphism at the Human Tumor Necrosis Factor (TNF) Locus," *J. Immunology* 147:1053–1059 (1991).

Plevy et al., "Increased Mucosal TNF–α mRNA Levels and Numbers of TNF–α Producing Cells are Unique to Crohn's Disease Musosal Inflammation," *Gastroenterology* 106:A754 (1994).

Plevy et al., "TNF–α mRNA Levels Differentiate Mucosal Inflammation in Crohn's Disease from Ulcerative Colitis," *J. Immunol.* 150:10A, abstract 41 (1993).

Plevy et al., "Tumor Necrosis Factor Microsatellites Define a Crohn's Disease–Associated Haplotype on Chromosome 6," *Gastroenterology* 110: 1053–1060 (1996).

Pociot et al., "Association of Tumor Necrosis Factor (TNF) and Class II Major Histocompatibility Complex Alleles with the Secretion of TNF–α and TNF–β by Human Mononuclear Cells: A Possible Link to Insulin–Dependent Diabetes Mellitus," *Eur. J. Immunol.* 23:224–231 (1993).

Sendid et al., "Specific Antibody Response to Oligomannosidic Epitopes in Crohn's Disease," *Clinical and Diagnostic Laboratory Immunology* 3:219–226 (1996).

Udalova et al., "Highly Informative Typing of the Human TNF Locus Using Six Adjacent Polymorphic Markers," *Genomics* 16:180–186 (1993).

Yang et al., "Linkage of Crohn's Disease to the HLA Region is Consistently Detected by Multiple Nonparametric Approaches," *Am. J. Human Genetics* 57:A233, abst. 1348 (1995).

Yang et al., "Ulcerative Colitis: A Genetically Heterogeneous Disorder Defined by Genetic (HLA Class II) and Subclinical (Antineutrophil Cytoplasmic Antibodies) Markers," *J. Clin. Invest.* 92:1080–1084 (1993).

Young et al., "Lymphocyte Proliferation Response to Baker's Yeast in Crohn's Disease," *Digestion* 55:40–43 (1994).

METHODS OF DIAGNOSING A MEDICALLY RESISTANT CLINICAL SUBTYPE OF ULCERATIVE COLITIS

This work was supported by USPHS grant DK46763 awarded by The United States Public Health Service. The United States government has certain rights in this invention.

BACKGROUND OF THE INVENTION

1. Field of the Invention

The invention relates generally to the fields of autoimmunity and inflammatory bowel disease and more specifically to serological and genetic methods for diagnosing clinical subtypes of ulcerative colitis.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Unfortunately, the available therapies for ulcerative colitis are limited in effectiveness, and both diagnosis and treatment have been hampered by a lack of knowledge regarding the etiology of the disease. What is clear, however, is that ulcerative colitis is a classification representing a number of distinct disease subtypes that affect the gastrointestinal tract and produce similar symptoms. The heterogeneity underlying UC is reflected in variable responses of UC patients to particular treatment strategies: available anti-inflammatory and steroid therapies are effective in treating some patients with UC, while other patients have disease that is resistant to medical treatment. Methods of diagnosing this medically resistant clinical subtype would be useful since these patients can benefit from early, aggressive treatment prior to full progression of their disease.

Methods for diagnosing the medically resistant clinical subtype of UC would represent a major clinical advance that would aid in the therapeutic management of UC. These diagnostic methods, combined with earlier medical treatment, would provide a patient having medically resistant disease with an alternative to surgical colectomy. Such methods also would advance medical management of UC by identifying a subgroup of patients for whom alternative treatment modalities must be sought. Unfortunately, methods of stratifying UC into medically resistant and medically responsive clinical subtypes are currently not available. Thus, there is a need for such methods. The present invention satisfies this need and provides related advantages as well.

SUMMARY OF THE INVENTION

The present invention provides serological and genetic methods of diagnosing a medically resistant clinical subtype of ulcerative colitis (UC). The invention provides a method of diagnosing a medically resistant clinical subtype of UC by determining the presence or absence of anti-*Saccharomyces cerevisiae* antibodies (ASCA) in a patient with UC, where the presence of ASCA indicates the medically resistant clinical subtype of UC.

The present invention also provides a method of diagnosing a medically resistant clinical subtype of UC by determining the presence or absence of a TNFa2b1c2d4e1 haplotype in a patient with UC, where the presence of the TNFa2b1c2d4e1 haplotype indicates the medically resistant clinical subtype of UC.

In addition, the invention provides a method of diagnosing a medically resistant clinical subtype of UC by determining the presence or absence of a TNFa2b1c2d4e1 haplotype in a patient with UC and determining the presence or absence of ASCA in the patient with UC, where the presence of the TNFa2b1c2d4e1 haplotype indicates the medically resistant clinical subtype of UC and the presence of ASCA independently indicates the medically resistant clinical subtype of UC.

The invention further provides kits for diagnosing a medically resistant clinical subtype of UC containing antigen specific for ASCA and one or more oligonucleotide primers complementary to a nucleotide sequence flanking one of the TNFa, TNFb, TNFc, TNFd or TNFe microsatellite loci. The kits can include, for example, antigen specific for ASCA and pairs of oligonucleotide primers complementary to nucleotide sequences flanking each of the TNFa, TNFb, TNFc, TNFd and TNFe loci. The antigen specific for ASCA can be, for example, yeast cell wall phosphopeptidomannan. If desired, one or more secondary antibodies selective for ASCA also can be included in the kits.

DETAILED DESCRIPTION OF THE INVENTION

The present invention provides a method of diagnosing a medically resistant clinical subtype of UC by determining the presence or absence of anti-*Saccharomyces cerevisiae* antibodies (ASCA) in a patient with UC, where the presence of ASCA indicates the medically resistant clinical subtype of UC.

Anti-*Saccharomyces cerevisiae* antibodies (ASCA) are characteristically elevated in patients having Crohn's disease although the nature of the *S. cerevisiae* antigen supporting the specific antibody response in CD is unknown (Sendid et al., *Clin. Diag. Lab. Immunol.*, 3:219–226 (1996), which is incorporated herein by reference). These antibodies may represent a response against yeasts present in common food or drink or a response against yeasts that colonize the gastrointestinal tract. Studies with periodate oxidation have shown that the epitopes recognized by ASCA in CD patient sera contain polysaccharides. Oligomannosidic epitopes are shared by a variety of organisms including different yeast strains and genera, filamentous fungi, viruses, bacteria and human glycoproteins. Thus, the mannose-induced antibody responses in CD may represent a response against a pathogenic yeast organism or may represent a response against a cross-reactive oligomannosidic epitope present, for example, on a human glycoprotein autoantigen. Regardless of the nature of the antigen, elevated levels of serum ASCA are a differential marker for Crohn's disease, with only low levels of ASCA reported in UC patients (Sendid et al., supra, 1996).

Provided herein are serological methods of diagnosing a medically resistant clinical subtype of ulcerative colitis. As described in Example I and summarized in Table 6, 19% of patients undergoing colectomy for medically resistant UC unresponsive to steroids, 5-aminosalicylic acid (5-ASA), 6-mercaptopurine (6-MP) and cyclosporin A were ASCA-positive, as compared with only 2.9% of UC patients with medically responsive disease who were positive for serum ASCA. Thus, the presence of ASCA in a patient with UC indicates an approximately 6-fold higher probability that a particular UC patient will be resistant to standard medical treatment. These results indicate that the presence of ASCA in a patient having UC is diagnostic of a medically resistant subtype of UC.

The methods and kits of the invention relate to ulcerative colitis, which is a disease of the large intestine characterized by chronic diarrhea with cramping abdominal pain, rectal bleeding, and loose discharges of blood, pus and mucus. The manifestations of this disease vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis, and especially long-standing, extensive disease, is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. Furthermore, the inflammatory process of UC is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerate intestinal crypts are filled with neutrophils, also are typical of the pathology of ulcerative colitis (Rubin and Farber, *Pathology* (Second Edition) Philadelphia: J. B. Lippincott Company (1994), which is incorporated herein by reference).

As used herein, the term "ulcerative colitis" is synonymous with "UC" and means a disease having clinical features of left-sided colonic disease accompanied by a characteristic endoscopic or histopathologic feature of UC. Clinical features of left-sided colonic disease, as used herein, are rectal bleeding, urgency and tenesmus. The rectal bleeding may be accompanied by mucus discharge. Additional clinical features that may be present in UC include treatment with topical therapy and recommended or performed total or near-total colectomy.

A characteristic endoscopic feature of UC, which when present with clinical features of left-sided colonic disease indicates ulcerative colitis, is inflammation that is more severe distally than proximally or continuous inflammation. Additional typical endoscopic features that may be present in UC include inflammation extending proximally from the rectum or shallow ulcerations or the lack of deep ulcerations.

TABLE 1

Clinical, endoscopic and histopathologic features of UC

| | |
|---|---|
| A. Clinical features of left-sided colonic disease | 1. Rectal bleeding possibly accompanied by mucus discharge |
| | 2. Urgency |
| | 3. Tenesmus |
| | 4. Treatment with topical therapy |
| | 5. Recommended or performed total or near-total colectomy |
| B. Endoscopic features of UC | 6. Inflammation that is more severe distally than proximally |
| | 7. Continuous inflammation |
| | 8. Inflammation extending proximally from the rectum |
| | 9. Shallow ulcerations or lack of deep ulcerations |
| C. Histopathologic features of UC | 10. Homogeneous, continuous, predominantly superficial inflammation |
| | 11. Lack of "focality" within biopsy specimens |
| | 12. Crypt abscesses |
| | 13. Lack of granulomas |

A characteristic histopathologic feature of UC, which when present with clinical features of left-sided colonic disease indicates ulcerative colitis, is homogeneous, continuous, predominantly superficial inflammation or a lack of "focality" within biopsy specimens. Additional typical histopathologic features that may be present in UC include the presence of crypt abscesses or a lack of granulomas. Characteristic clinical features of left-sided colonic disease and characteristic endoscopic and histopathologic features of ulcerative colitis are summarized in Table 1.

Patients with medically responsive ulcerative colitis have disease that is ameliorated by an available medical therapy. Patients with mild or moderate UC may respond to anti-inflammatory aminosalicylates such as 5-aminosalicylic acid (5-ASA), and patients with more severe disease may respond to corticosteroid treatment. Extensive mild or moderate disease can be treated with oral therapy while topical therapy can be used to treat distal colitis. Parenteral corticosteroid or intravenous cyclosporine treatment are therapeutic options for patients with fulminant disease. Patients in remission are maintained on medications such as aminosalicylates or oral azathioprine or mercaptopurine. The side effects of such chronic steroid treatment and immunosuppressive drugs are significant, especially in children and older patients (see Hanauer and D'Haens, In: Targan and Shanahan, *Inflammatory Bowel Disease; From Bench to Bedside* Williams and Wilkens, 1994, pp 545–560; and Hanauer, *New Engl. J. Med.* 334(13): 841–848 (1996), each of which is incorporated herein by reference.

Ulcerative colitis is cured by colectomy, although this is a radical treatment even with newly developed procedures to maintain continence. An alternative disclosed herein is a diagnostic method for the early determination of medically resistant UC. Patients having this clinical subtype of UC, which ultimately will progress to the point where it is no longer responsive to medical treatment with drugs such as aminosalicylates, corticosteroids, 5-azathioprine or 6-mercaptopurine, can benefit from early, aggressive treatment prior to development of refractory inflammation.

The present invention provides a method of diagnosing a medically resistant clinical subtype of UC by obtaining a sample from a patient with UC, contacting the sample with antigen specific for ASCA under conditions suitable to form a complex of the antigen specific for ASCA and antibody to the antigen, and detecting the presence or absence of said complex, where the presence of the complex indicates the medically resistant clinical subtype of UC.

As used herein, the term "patient with UC" means a patient having ulcerative colitis, as defined by the presence of clinical features of left-sided colonic disease accompanied by a characteristic endoscopic or histopathologic feature of UC as defined herein. A patient refers to any animal capable of having ulcerative colitis including, for example, a human, non-human primate, rabbit, rat or mouse.

The term "clinical subtype of UC," as used herein, means a subgroup of patients having ulcerative colitis whose features of disease are more similar to each other than to other patients with ulcerative colitis.

The term "medically resistant clinical subtype of UC" means a subgroup of UC patients with disease that is resistant to standard regiments of treatment. For example, a medically resistant clinical subtype of UC is unresponsive to steroids, 5-aminosalicylic acid (5-ASA), 6-mercaptopurine (6-MP), cyclosporine A, and the like. As a result of such resistance to standard treatments, this subgroup of UC patients typically require more aggressive forms of medical treatment or colectomy.

Certain immune-mediated disorders, including systemic lupus erythematosis, primary biliary cirrhosis and autoimmune hepatitis, are closely associated with distinctive patterns of autoantibody production. Such autoantibodies, which may be fundamental to pathogenesis of disease or secondary to inflammation, can be diagnostic of a particular disease or disease subtype.

Anti-*Saccharomyces cerevisiae* antibodies (ASCA), as described above, are a serum marker characteristically elevated in patients with Crohn's disease but not in UC. As disclosed herein, ASCA antibodies can be used to diagnose a medically resistant clinical subtype of UC. The results set forth in Example I indicate that serum ASCA are significantly more prevalent in UC patients undergoing colectomy for medically resistant UC unresponsive to steroids, 5-ASA, 6-MP and cyclosporine A, as compared to UC patients who respond to these medications.

As used herein, the term "antigen specific for ASCA" refers to any antigen or mixture of antigens that is bound specifically by ASCA. Although ASCA antibodies were initially characterized by their ability to bind *S. cerevisiae*, those of skill in the art will understand that an "antigen specific for ASCA" can be obtained from *S. cerevisiae*, or can be obtained from a variety of other sources so long as the antigen is capable of binding specifically to ASCA antibodies. Accordingly, exemplary sources of an antigen specific for ASCA contemplated for use in the methods of the invention include whole killed yeast cells, such as from the genera Saccharomyces and Candida, yeast cell wall phosphopeptidomannan (PPM), oligomannosides, neoglycolipids, anti-ASCA idiotypic antibodies, and the like. As described above, different species and strains of yeast, including Saccharomyces, can be used as an antigen specific for ASCA in the methods provided herein. For example, *S. cerevisiae* strain Su1, Su2, CBS 1315 or BM 156, or *Candida albicans* strain VW32, can be used as an antigen specific for ASCA in the methods of the invention.

Preparations of yeast cell wall mannans, or phosphopeptidomannans (PPM), are also contemplated herein as antigens specific for ASCA. These water soluble surface antigens can be prepared by appropriate extraction techniques, including autoclaving as described in Example II or can be obtained commercially (see Lindberg et al., *Gut* 33:909–913 (1992), which is incorporated herein by reference). The acid stable fraction of yeast cell wall PPM also can be useful in the methods of the invention (Sendid et al., supra, 1996). An exemplary PPM for use in diagnosing a medically resistant clinical subtype of UC is derived from *S. uvarum* strain ATCC #38926.

Purified oligosaccharide antigens, such as oligomannosides specific for ASCA, also are contemplated for use in the methods of the invention. For use herein, the purified oligomannoside antigens are preferably converted into neoglycolipids as described in Faille et al., *Eur. J. Microbiol. Infect. Dis.* 11:438–446 (1992). One skilled in the art understands that the reactivity of such an oligomannoside antigen with ASCA can be optimized by varying the mannosyl chain length (Frosh et al., *Proc. Natl. Cad. Sci. USA*, 82:1194–1198 (1985)); the anomeric configuration (Fukazawa et al., In E. Kurstak (ed.), *Immunology of Fungal Disease*, Marcel Dekker Inc., New York, pp. 37–62 (1989); Nishikawa et al, *Microbiol. Immunol.*, 34:825–840 (1990); Poulain et al., *Eur. J. Clin. Microbiol,* 23:46–52 (1993); Shibata et al., *Arch. Biochem. Biophys.*, 243:338–348 (1985); and Trinel et al., *Infect. Immun.*, 60:3845–3851 (1992)); or the position of the linkage (Kikuchi et al., *Planta*, 190:525–535 (1993)). Each of the foregoing references are incorporated herein by reference in their entirety.

In a particular embodiment of the present invention, an oligomannoside antigen specific for ASCA includes the mannotetraose Man($1\rightarrow3$)Man($1\rightarrow2$)Man($1\rightarrow2$)Man, and can be purified from PMM as described in Faille et al., supra, 1992. An exemplary neoglycolipid for use in the invention methods can be constructed by releasing the oligomannoside from its respective PPM and subsequently coupling the released oligomannoside to 4-hexadecylaniline or the like, as set forth in Example III.

As used herein, the term "sample" means any biological fluid or tissue having ASCA such as, for example, whole blood, plasma or other bodily fluid or tissue having ASCA, preferably serum.

As used herein, the term "complex" is synonymous with "immune complex" and means an aggregate of two or more molecules that results from specific binding between an antibody and an antigen, such as an oligomannoside, peptide or protein. For example, a complex can be formed by specific binding of ASCA to PPM.

As used herein, the term "antibody" means a population of immunoglobulin molecules, which can be polyclonal or monoclonal and of any isotype. As used herein, the term antibody encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

As used herein, the term "secondary antibody" means an antibody or combination of antibodies, which binds ASCA of UC. Preferably, a secondary antibody does not compete with antigen for binding to ASCA. A secondary antibody can be, however, an anti-ASCA antibody that binds any epitope of ASCA. A particularly useful secondary antibody is an anti-IgA antibody or anti-Ig antibody, or combination thereof, having specificity for the class determining portion of ASCA. One skilled in the art understands that a useful secondary antibody is specific for the species of the ASCA to be detected. For example, if human serum is the sample to be assayed, mouse anti-human IgA can be a useful secondary antibody. A combination of different antibodies, which can be useful in the methods of the invention, also is encompassed within the meaning of the term secondary antibody, provided that at least one antibody of the combination binds ASCA of UC.

A monoclonal antibody useful in the practice of the invention can be obtained from a number of commercially available sources. In addition, an immunogen useful to generate a monoclonal antibody that binds ASCA selectively can be, for example, human IgA or a Fc fragment of human IgA, or a Fab fragment of ASCA. A hybridoma that produces a monoclonal selective for ASCA can be identified by screening hybridoma supernatants for the presence of antibodies that bind ASCA specifically (Harlow and Lane, *Antibodies: A Laboratory Manual* New York: Cold Spring Harbor Laboratory (1988). For example, such a screening method can be a radioimmunoassay or enzyme-linked immunosorbent assay using PPM prepared from *S. uvarum* strain ATCC #38926 and ASCA-positive sera, for example.

A secondary antibody useful in the invention can be obtained commercially or by techniques well known in the art. Such an antibody can be a polyclonal or, preferably, monoclonal antibody that binds ASCA. For example, IgA reactive polyclonal antibodies can be prepared using IgA or Fc fragments of IgA as an immunogen to stimulate the production of antibodies in the antisera of an animal such as a rabbit, goat, sheep or rodent, as described in Harlow and Lane, *Antibodies: A Laboratory Manual* New York: Cold Spring Harbor Laboratory (1988), which is incorporated herein by reference.

As used herein, the term "class determining portion" when used in reference to a secondary antibody, means the heavy chain constant-region sequence of an antibody that determines the isotype, such as IgA, IgD, IgE, IgG or IgM. Thus, a secondary antibody that has specificity for the class determining portion of an IgG molecule, for example, binds IgG in preference to other antibody isotypes.

The term "detectable secondary antibody" means a secondary antibody, as defined above, that can be detected or measured by analytical methods. Thus, the term secondary antibody includes an antibody labeled directly or indirectly with a detectable marker that can be detected or measured and used in a convenient assay such as an enzyme-linked immunosorbent assay, radioimmunoassay, radial immunodiffusion assay or Western blotting assay. A secondary antibody can be labeled, for example, with an enzyme, radioisotope, fluorochrome or chemiluminescent marker. In addition, a secondary antibody can be rendered detectable using a biotin-avidin linkage such that a detectable marker is associated with the secondary antibody. Labeling of the secondary antibody, however, should not impair binding of the secondary antibody to ASCA of UC. If desired, a multiple antibody system can be used as the secondary antibody as discussed above. In such a system, at least one of the antibodies is capable of binding ASCA of UC and at least one of the antibodies can be readily detected or measured by analytical methods.

Methods of determining the presence or absence of ASCA are well known in the art (Harlow and Lane, *Antibodies: A Laboratory Manual* New York: Cold Spring Harbor Laboratory (1988), which is incorporated herein by reference). For example, ASCA can be detected in patient sera using a detectable reagent such as a secondary antibody labeled with a detectable enzymatic, radioisotopic, fluorescent or chemiluminescent market. Particularly useful methods include a quantitative assay such as an immunoassay, in which an antibody selective for ASCA is used to detect ASCA in patient sera. Radioimmunoassays (RIA) and enzyme-linked immunosorbent assays (ELISA), for example, are encompassed within the invention.

An enzyme-linked immunosorbent assay (ELISA) can be useful in determining whether ASCA is present in patient sera. For example, an ELISA for detection of ASCA in UC patient sera is described in Example II. An enzyme that is linked to a secondary antibody selective for ASCA can be, for example, horseradish peroxidase (HRP), alkaline phosphatase (AP), β-galactosidase or urease. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm, or a urease detection system can be used with a substrate such as urea-bromocresol purple (Sigma Immunochemicals, St. Louis, Mo.). A secondary antibody linked to an enzyme is a detectable reagent useful in an ELISA and can be obtained from a number of commercial sources. For example, goat $F(ab')_2$ anti-human IgG conjugated to alkaline phosphatase can be purchased from Pierce (Rockford, Ill.) and similarly IgA can be purchased from Jackson Immunoresearch (Westgrove, Pa.).

In the methods of the invention for diagnosing a medically resistant subtype of UC, a radioimmunoassay also can be useful in determining whether ASCA is present in patient sera. A radioimmunoassay using, for example, an iodine-125 labeled secondary antibody (Harlow and Lane, supra, 1988) is encompassed within the invention.

A secondary antibody labeled with a chemiluminescent marker also can be useful for determining whether ASCA is present in UC patient sera. Such a chemiluminescent secondary antibody is convenient for sensitive, non-radioactive detection of ASCA and can be obtained commercially from various sources such as Amersham Lifesciences, Inc. (Arlington Heights, Ill.).

In addition, a detectable reagent labeled with a fluorochrome can be useful in determining whether ASCA is present in patient sera. Appropriate fluorochromes include, for example, DAPI, fluorescein, Hoechst 33258, R-phycocyanin, B-phycoerythrin, R-phycoerythrin, rhodamine, Texas red or lissamine. A particularly useful fluorochrome is fluorescein or rhodamine. A secondary antibody linked to a fluorochrome is a particularly useful detectable reagent and can be obtained commercially. For example, goat F(ab')2 anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of iodine-125; or a fluorometer to detect fluorescence in the presence of light of a certain wavelength. For detection of enzyme-linked reagents, a quantitative analysis of the amount of ASCA can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The present invention also provides a genetic method of diagnosing a medically resistant clinical subtype of UC by determining the presence or absence of a TNF microsatellite allele selected from the group consisting of TNFa2, TNFb1, TNFc2, TNFd4 and TNFe1 in a patient with UC, where the presence of one or more of the TNF microsatellite alleles indicates a medically resistant clinical subtype of UC.

The present also provides a method of diagnosing a medically resistant clinical subtype of UC by determining the presence or absence of at least two TNF microsatellite alleles selected from the group consisting of TNFa2, TNFb 1, TNFc2, TNFd4 and TNFe1 in a patient with UC, where the presence of an allelic combination containing at least two of the alleles indicates a medically resistant clinical subtype of UC.

The allelic combination can contain at least three of the alleles selected from the group consisting of TNFa2, TNFb1, TNFc2, TNFd4 and TNFe1. For example, the allelic combination can include the three microsatellite alleles TNFa2, TNFb1 and TNFc2. The allelic combination also can include four microsatellite alleles such as TNFa2, TNFb 1, TNFc2 and TNFd4 or such as TNFa2, TNFb1, TNFc2 and TNFe1. In addition, the allelic combination can include five microsatellite alleles.

The present invention also provides a method of diagnosing a medically resistant clinical subtype of UC by determining the presence or absence of a TNFa2b1c2d4e1 haplotype in a patient with UC, where the presence of said TNFa2b1c2d4e1 haplotype indicates the medically resistant clinical subtype of UC.

As set forth in Example I, the TNFa2b1c2d4e1 haplotype is significantly more frequent in patients with medically resistant UC who require colectomy (32%) than in patients who respond to one of these medications (8.7%). These results, which are summarized in Table 6, indicate that the presence of the TNFa2b1c2d4e1 haplotype is diagnostic of a medically resistant clinical subtype of UC in a patient having UC. Thus, according to the methods of the invention, the medically resistive clinical subtype of UC can be diagnosed by genetics markers as well as serological ones.

The human genome contains a large number of interspersed simple tandem repeat sequences, designated microsatellites, which vary in length among individuals and therefore serve as highly informative polymorphic markers. Although the function of these regions is unknown, there are 50,000 to 100,000 microsatellite sequence repeats throughout the human genome. This abundant class of DNA polymorphisms can be typed, for example, using the polymerase chain reaction (PCR), as described further below. In particular, five polymorphic TNF microsatellite loci, denoted TNFa, TNFb, TNFc, TNFd and TNFe, have been described in association with the TNF-α and TNF-β genes.

Host genetic factors can confer susceptibility or resistance to tissue damage elicited by a chronic local immune response. For example, IBD is associated with polymorphisms in MHC class II, ICAM-1 and TNF-α loci (Yang et al., *J. Clin. Invest.* 92:1080–1084 (1993)), and animal and clinical studies directly implicate TNF levels in disease. TNF microsatellite haplotypes containing the TNFa2 allele have been suggested to be of particular relevance in inflammatory bowel disease because a TNFa2-containing haplotype associated with insulin-dependent diabetes mellitus correlated with increased TNF-α secretory capacity (Pociot et al., *Eur. J. Immunol.* 23:224–231 (1993), which is incorporated herein by reference). Recent work has shown that the three-locus combination TNFa2b1c2 is more frequently present in patients with CD (25.3%) than in patients with UC (5.5%; p=0.0009) as described in Plevy et al., *Gastroenterol,* 110:1053–1060 (1996), which is incorporated herein by reference. Furthermore, the TNFa2b1c2d4e1 haplotype is present more frequently in patients with CD (24%) than in patients with UC (4.1%) or non-inflammatory bowel disease controls (6.7%; p=0.001; see Plevy et al., supra, 1996). These studies indicate that the a2b1c2d4e1 haplotype can be diagnostic of Crohn's disease and is only infrequently associated with ulcerative colitis. The present invention is directed to the surprising discovery that the presence of the TNFa2b1c2d4e1 haplotype in a patient with UC is diagnostic of a medically resistant subtype of UC.

As used herein, the term "microsatellite allele" means a nucleotide sequence that is distinguished by its number of nucleotide or dinucleotide repeats from an alternative nucleotide sequence which occupies the same chromosomal locus. As used herein, the term "TNF microsatellite allele" refers to a microsatellite allele at one of the TNFa, TNFb, TNFc, TNFd or TNFe loci.

Figure 1:
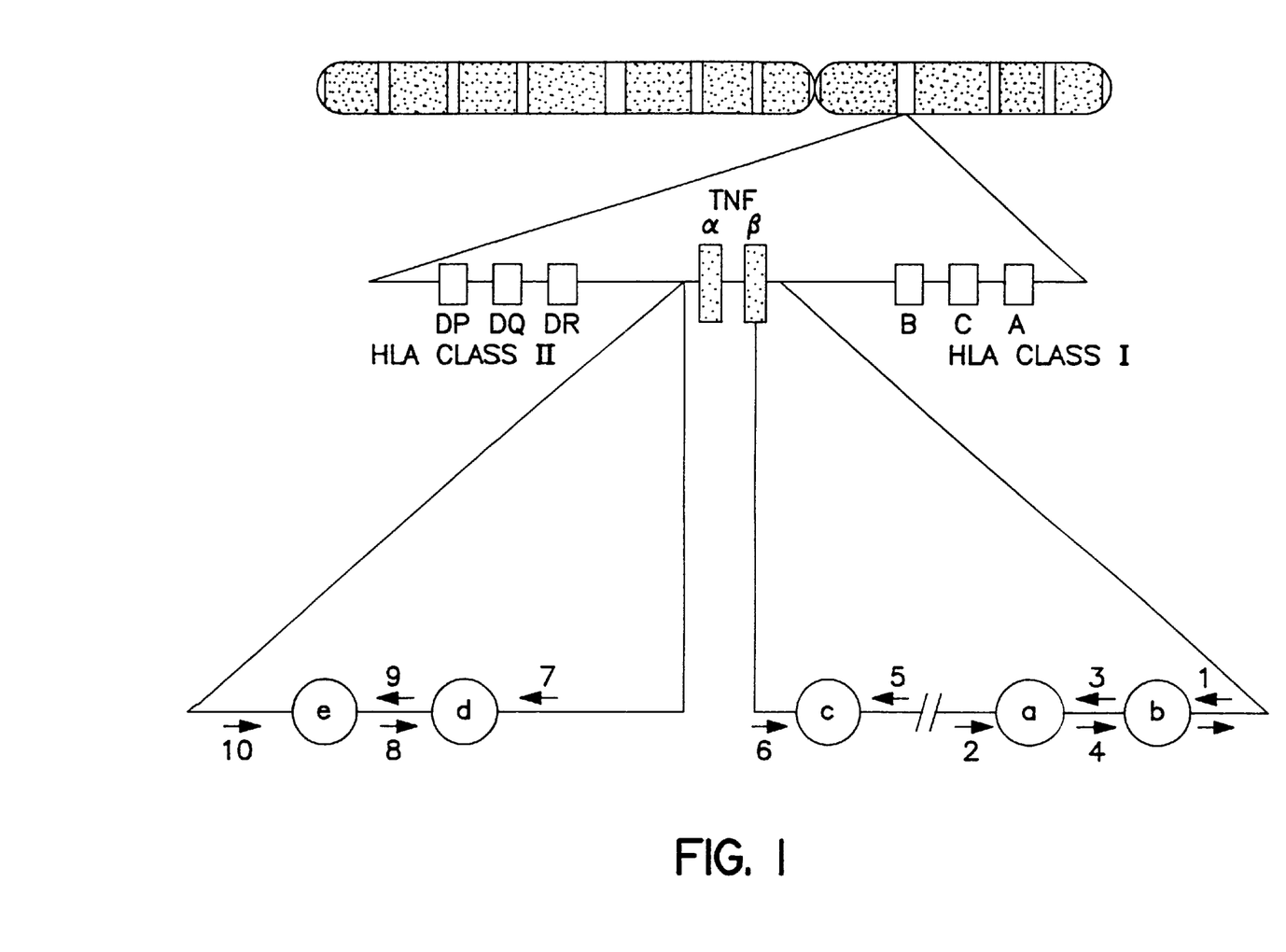
FIG. 1 shows the relative location of the five TNF microsatellite loci: TNFa, TNFb, TNFC, TNFd and TNFe. Also shown are the relative locations of oligonucleotide primers SEQ ID NOS: 1 to 10, with orientation indicated by numbered arrows.

The relative locations of the five TNF microsatellite loci are shown in FIG. 1. The TNFa and TNFb are closely linked and located 3.5 kb upstream of the TNF-β gene. TNFa microsatellites are characterized by AC/GT dinucleotide repeats, and TNFb microsatellites are characterized by TC/GA sequences that differ by 1 or 2 bases. TNF microsatellite c, which is located within the intron of the TNF-β gene, is characterized by TC/GA dinucleotide sequence repeats. TNFd and TNFe are located 8 to 10 kb downstream of the TNF-α gene. TNFd is characterized by TC/GA-like sequence repeats, which are similar to TC/GA repeats except that the repeats are interrupted by an extra base pair. TNFe is characterized by TC/GA dinucleotide sequence repeats. These TNF microsatellite loci have been described in Nedospasov et al., *J. Immunol.* 147:1053–1059 (1991), Jongeneel et al., *Proc. Natl. Acad. Sci. USA* 88:9717–9721 (1991) and Udalova et al., *Genomics* 16:180–186 (1993), each of which is incorporated herein by reference.

As used herein, the term "allelic combination" means a particular combination of alleles at two or more TNF microsatellite loci. An allelic combination can involve particular alleles at two, three, four or five TNF microsatellite loci.

As used herein, the term "TNF microsatellite haplotype" means a five-locus allelic combination defined by particular alleles at the TNFa, TNFb, TNFc, TNFd and TNFe loci. The term "TNFa2b1c2d4e1 haplotype" is synonymous with "a2b1c2d4e1 haplotype" and means a TNF microsatellite haplotype defined by the combination of the TNFa2 allele, TNFb1 allele, TNFc2 allele, TNFd4 allele and TNFe1 allele. A patient who is "a2b1c2d4e1-positive" has the a2b1c2d4e1 haplotype.

The presence or absence of a TNF microsatellite allele can be determined using a variety of methods well known in the art. Such methods are based on the unique length or nucleotide sequence of a particular microsatellite allele, where the unique length or nucleotide sequence distinguish that allele from other alleles at the same locus. For example, TNF microsatellite alleles of a single locus can be distinguished based on the size of an amplified product prepared with flanking primers relative to amplification of nucleic acid having a known TNF microsatellite allele (see Example IV; see, also, Udalova et al., supra, 1993). Microsatellite alleles differ by one dinucleotide repeat for TNFa, TNFc, TNFd, and TNFe. For TNFb, alleles differ by 1 or 2 bases as reported in Udalova et al., supra, 1993. Sequence analysis, including automated sequence analysis, also can be useful in determining whether a particular TNF microsatellite allele is present, as described further below. In addition, assays such as allele-specific oligonucleotide hybridization can be used to determine whether a particular TNF microsatellite allele is present in a patient having UC (see Mullis et al. (ed.), *The Polymerase Chain Reaction* Boston: Birkhäuser (1994), which is incorporated herein by reference). Well known electrophoretic methods such as denaturing gradient gel electrophoresis also are useful in the methods of the invention (see, for example, Innis et al., *PCR Protocols: A Guide to Methods and Application,* San Diego: Academic Press, Inc. (1990), which is incorporated herein by reference).

The present invention also provides a method of diagnosing a medically resistant clinical subtype of UC by determining the presence or absence of a TNFa2b1c2d4e1 haplotype in a patient with UC by obtaining material having nucleic acid including the TNFa, TNFb, TNFc, TNFd and TNFe loci from the patient; enzymatically amplifying the nucleic acid using pairs of oligonucleotide primers complementary to nucleotide sequences flanking each of the TNFa, TNFb, TNFc, TNFd and TNFe loci to produce amplified products including TNFa, TNFb, TNFc, TNFd or TNFe; and electrophoresing the amplified products to identify the TNFa2b1c2d4e1 haplotype.

As used herein, the term "material" means any biological matter from which nucleic acid can be prepared. For example, the term material encompasses whole blood, plasma or other bodily fluid or tissue that contains nucleic acid. A preferred material is patient sera, which can be obtained readily by non-invasive means and used to prepare genomic DNA for the diagnosis of a medically resistant clinical subtype of UC according to the methods of the invention.

As used herein, the term "nucleic acid" means a polynucleotide such as deoxyribonucleic acid (DNA). A nucleic acid can be either single-stranded or double-stranded. One skilled in the art can practice the methods of the invention with a nucleic acid such as genomic DNA.

The term "enzymatically amplifying," as used herein in reference to a nucleic acid including one or more of the five TNF microsatellite loci, means an enzymatic process whereby, from an initial amount of nucleic acid including or more of the five TNF microsatellite loci, a larger amount of nucleic acid containing some or all of the same nucleic acid sequence is produced. The polymerase chain reaction (PCR), which involves the use of a thermo-stable DNA polymerase and repeated cycles of polymerization, is particularly useful in the methods of the invention. PCR is well known in the art as described, for example in Mullis et al., supra, 1994, and Innis et al., supra, 1990. As used herein, the term "amplified product" means nucleic acid produced by the process of enzymatic amplification.

The term "oligonucleotide primers complementary to nucleotide sequences flanking each of the TNFa, TNFb, TNFc, TNFd and TNFe loci," as used herein, means linear oligonucleotides of about ten to about fifty nucleotides in length that are complementary to nucleotide sequences 5' or 3' of a TNF locus to be amplified. One can use, for example, a pair of oligonucleotide primers in which one of the primers is complementary to a nucleotide sequence 5' of the TNF microsatellite locus or loci to be amplified while the other primer of the pair is complementary to a nucleotide sequence located 3' of the TNF microsatellite locus or loci to be amplified. One skilled in the art understands that a pair of oligonucleotide primers means two oligonucleotides complementary to opposite strands of nucleic acid and flanking the locus to be amplified.

Primers suitable for use in amplifying nucleic acid including TNF microsatellite loci TNFa, TNFb, TNFc, TNFd or TNFe can be generated according to the sequences described herein or using the map and sequence of the TNF locus available from Genbank as part of the human genome project funded through the National Institute of Health and incorporated herein by reference. The map and sequence of the TNF locus can be readily obtained for example, on the internet world wide web at http://www.ncbi.nlm.nih.gov. NCBI's database is incorporated herein in its entirety. Primers useful in the methods of the invention can have, for example, a length of about 12, 15, 17, 20 or 25 nucleotides. Exemplary oligonucleotide primers complementary to nucleotide sequences flanking the five TNF loci are described further below.

For use in the methods of the invention, one skilled in the art understands that an oligonucleotide primer complementary to a nucleotide sequence flanking a TNF locus is relatively specific for amplification of nucleic acid including the TNF microsatellite locus to be amplified. For example, when the presence of a particular TNF microsatellite allele is to be determined by sequence analysis, an oligonucleotide primer preferably is complementary only to a nucleotide sequence flanking the TNF locus to be amplified. However, when the presence of a particular TNF microsatellite allele is determined based on the size of the amplified product, an oligonucleotide primer can be complementary to other unrelated sequences in addition to the nucleotide sequence flanking the TNF locus to be amplified. In this case, one or more amplified products unrelated to the TNF locus may be produced in addition to the amplified product of interest. However, for such a primer to be useful, one skilled in the art understands that the size of the one or more unrelated amplified products must be distinct from the size of the amplified product including the TNF locus.

FIG. 1 shows the relative location and orientation of primers with regard to TNF microsatellite loci, and Table 7 shows the primer sequences. Oligonucleotide primers complementary to a nucleotide sequence flanking TNFa and TNFb are SEQ ID NOS: 1 and 2. These oligonucleotide primers can be used together as a pair or in combination with another suitable oligonucleotide primer to amplify genomic DNA including TNFa and TNFb. SEQ ID NO: 1 is complementary to a nucleotide sequence 5' of TNFb, and SEQ ID NO: 2 is complementary to a nucleotide sequence 3' of TNFa. If desired, nucleic acid including the TNFa locus can be individually amplified without amplifying TNFb. For example, SEQ ID NOS: 2 and 3 can be used as a primer pair for amplification of the TNFa locus. Similarly, one can amplify nucleic acid including the TNFb locus without amplifying the TNFa locus.

SEQ ID NOS: 5 and 6 are oligonucleotide primers that can be used to amplify genomic DNA that includes TNFc. Primers SEQ ID NOS: 5 and 6 can be used as a pair or each in combination with another suitable primer. As depicted in FIG. 1, SEQ ID NO: 5 is complementary to a nucleotide sequence located 5' of the TNFc locus, and SEQ ID NO: 6 is complementary to a nucleotide sequence located 3' of the TNFc locus.

TABLE 2

Characterization of TNFa alleles
with primers SEQ ID NO: 2 and SEQ ID NO: 3

| Allele | Repeat Sequence | Number of Repeats | Size (bp) |
| --- | --- | --- | --- |
| TNFa1 | AC/GT | 6 | 98 |
| TNFa2 | AC/GT | 7 | 100 |

TABLE 2-continued

Characterization of TNFa alleles
with primers SEQ ID NO: 2 and SEQ ID NO: 3

| Allele | Repeat Sequence | Number of Repeats | Size (bp) |
|---|---|---|---|
| TNFa3 | AC/GT | 8 | 102 |
| TNFa4 | AC/GT | 9 | 104 |
| TNFa5 | AC/GT | 10 | 106 |
| TNFa6 | AC/GT | 11 | 108 |
| TNFa7 | AC/GT | 12 | 110 |
| TNFa8 | AC/GT | 13 | 112 |
| TNFa9 | AC/GT | 14 | 114 |
| TNFa10 | AC/GT | 15 | 116 |
| TNFa11 | AC/GT | 16 | 118 |
| TNFa12 | AC/GT | 17 | 120 |
| TNFa13 | AC/GT | 18 | 122 |

Primers SEQ ID NO: 7 and 10 are suitable for use in amplifying genomic DNA including TNFd and TNFe and can be used as a pair or each in combination with another suitable primer. SEQ ID NO: 7 is complementary to a nucleotide sequence 5' of TNFd, as depicted in FIG. 1, and SEQ ID NO: 10 is complementary to a nucleotide sequence 3' of TNFe. One also can amplify nucleic acid encoding the alleles of TNFd or TNFe separately: for example, SEQ ID NOS: 7 and 8 can be used as a primer pair to amplify nucleic acid including TNFd alleles, and SEQ ID NO: 9 and 10 can be used as a primer pair to amplify nucleic acid including TNFe alleles. FIG. 1 depicts the relative location and orientation of these primers in relation to TNF microsatellite loci.

TNF microsatellite a (TNFa) has at least thirteen alleles designated TNFa1 through TNFa13. Each of the TNFa alleles, which are characterized by a particular number of AC/GT dinucleotide sequence repeats, have a characteristic size when amplified by a particular pair of flanking primers. For each TNFa allele, the size of the amplified nucleic acid product generated with primers SEQ ID NO: 2 and SEQ ID NO: 3 is shown in Table 2.

TNF microsatellite b (TNFb) has at least seven alleles designated TNFb1 through TNFb7. Each of these alleles has a characteristic number of TC/GA dinucleotide sequence repeats ranging from 8 to 20 repeats and a characteristic size when amplified with a particular pair of flanking primers. Table 3 indicates the name, type of sequence repeat and size of each TNFb allele produced by flanking primers SEQ ID NO: 1 and SEQ ID NO: 4.

TNF microsatellite c (TNFc) has at least two alleles, which are designated TNFc1 and TNFc2. When amplified with flanking primers SEQ ID NO: 5 and SEQ ID NO: 6, TNFc1, which is characterized by a series of nine TC/GA dinucleotide sequence repeats, is 160 base pairs in size. TNFc2, which is characterized by a series of ten TC/GA dinucleotide sequence repeats, is 162 base pairs in size when amplified with primers SEQ ID NO: 5 and SEQ ID NO: 6.

TABLE 3

Characterization of TNFb alleles
with primers SEQ ID NO: 1 and SEQ ID NO: 4

| Allele | Repeat Sequence | Size (bp) |
|---|---|---|
| TNFb1 | TC/GA | 127 |
| TNFb2 | TC/GA | 128 |
| TNFb3 | TC/GA | 129 |
| TNFb4 | TC/GA | 130 |
| TNFb5 | TC/GA | 131 |
| TNFb6 | TC/GA | 132 |
| TNFb7 | TC/GA | 133 |

The TNF microsatellite d locus (TNFd) has at least seven alleles designated TNFd1 through TNFd7. Each of the TNF microsatellite d alleles has a characteristic size when amplified with primers SEQ ID NO: 7 and SEQ ID NO: 8 as shown in Table 4.

TABLE 4

Characterization of TNFd alleles
with primers SEQ ID NO: 7 and SEQ ID NO: 8

| Allele | Repeat Sequence | Size (bp) |
|---|---|---|
| TNFd1 | TC/GA-like | 124 |
| TNFd2 | TC/GA-like | 126 |
| TNFd3 | TC/GA-like | 128 |
| TNFd4 | TC/GA-like | 130 |
| TNFd5 | TC/GA-like | 132 |
| TNFd6 | TC/GA-like | 134 |
| TNFd7 | TC/GA-like | 136 |

The TNF microsatellite e locus (TNFe) has at least four alleles denoted TNFe1 through TNFe4. TNFe1 is 99 base pairs in size and is further characterized by a series of TC/GA sequence repeats. TNFe2 is 101 base pairs in size and is further characterized by a series of TC/GA sequence repeats. TNFe3 is 103 base pairs in size and is characterized by a series of TC/GA sequence repeats. TNFe4, which has not yet been identified in humans, is 105 base pairs in size and characterized by a series of TC/GA sequence repeats.

Positive controls for TNF microsatellite haplotypes a2b1c2d4e1 can be useful in determining whether these haplotypes are present in a patient with CD. A convenient positive control can be a cell line known to have the TNF microsatellite haplotype of interest, such as those described in Udalova et al., supra, 1993. A positive control for the presence of the a2b1c2d4e1 haplotype can be, for example, cell line DKB, MADURA, BOLETH, BSM, AMALA, LZL, MLF, JHAP, PMG075, H0301, MZ070782, LWAGS or another cell line known to have the a2b1c2d4e1 haplotype (see Table 5). These cell lines are readily available from the American Society of Histocompatibility and Immunogenetics Workshop (ASHI) or the Center for Human Polymorphism Studies (CEPH).

TABLE 5

Positive controls for the a2b1c2d4e1 haplotype

| Cell line | ASHI accession number | CEPH accession number |
|---|---|---|
| DKB | 9075 | ws54 |
| MADURA | 9069 | ws25 |
| BOLETH | 9031 | ws30 |
| BSM | 9032 | ws68 |
| AMALA | 9064 | ws37 |
| LZL | 9099 | — |
| MLF | 9091 | ws42 |
| JHAP | 9030 | ws39 |

TABLE 5-continued

Positive controls for the a2b1c2d4e1 haplotype

| Cell line | ASHI accession number | CEPH accession number |
|---|---|---|
| PMG075 | 9078 | — |
| H0301 | 9055 | ws11 |
| MZ070782 | 9002 | ws35 |
| LWAGS | 9079 | — |

One skilled in the art understands the importance of determining an allele unambiguously by comparison to a positive control. It is well known that particular alleles can migrate with an anomalous molecular weight. For example, TNFc1 and TNFc2, which are 160 and 162 bp in size, respectively, can migrate as fragments of 161.5 bp and 163.5 bp, respectively, when analyzed on an automated sequencer such as Applied Biosystem's 373 DNA Sequencer. Similarly, the seven TNFd alleles, which are reported to be 124 bp to 136 bp in size, can have apparent molecular weights of 126 bp to 138 bp when analyzed using automated sequencing.

The present invention further provides a method of diagnosing a medically resistant clinical subtype of UC by determining the presence or absence of a TNFa2b1c2d4e1 haplotype in a patient with UC by obtaining material comprising nucleic acid including TNFa, TNFb, TNFc, TNFd and TNFe loci from the patient; enzymatically amplifying the nucleic acid using pairs of oligonucleotide primers complementary to nucleotide sequences flanking each of the TNFa, TNFb, TNFc, TNFd and TNFe loci to produce amplified products including TNFa, TNFb, TNFc, TNFd or TNFe; and sequencing the amplified products to identify the TNFa2b1c2d4e1 haplotype.

The term "sequencing," as used herein, means a process for determining the order of nucleotides in a nucleic acid. A variety of methods for sequencing nucleic acids are well known in the art. Such sequencing methods include the Sanger method of dideoxy-mediated chain termination as described, for example, in Sanger et al., *Proc. Natl. Acad. Sci.* 74:5463 (1977), which is incorporated herein by reference (see, also, "DNA Sequencing" in Sambrook et al. (eds.), *Molecular Cloning: A Laboratory Manual* (Second Edition), Plainview, N.Y.: Cold Spring Harbor Laboratory Press (1989), which is incorporated herein by reference). A variety of polymerases including the Klenow fragment of *E. coli* DNA polymerase I; Sequenase™ (T7 DNA polymerase); Taq DNA polymerase and Amplitaq can be used in enzymatic sequencing methods. Well known sequencing methods also include Maxam-Gilber chemical degradation of DNA (see Maxam and Gilbert, Methods Enzymol. 65:499 (1980), which is incorporated herein by reference, and "DNA Sequencing" in Sambrook et al., supra, 1989).

One skilled in the art understands that an amplified product can be sequenced directly or subcloned into a vector prior to sequence analysis. Commercially available sequencing kits including the Sequenase™ kit from Amersham Life Science (Arlington Heights, Ill.) can be used to sequence an amplified product in the methods of the invention. Automated sequence analysis also can be useful, and automated sequencing instruments such as the Prism 377 DNA Sequencer or the 373 DNA Sequencer are commercially available, for example, from Applied Biosystems (Foster City, Calif.; see, also, Frazier et al., *Electrophoresis* 17:1550–1552 (1996), which is incorporated herein by reference).

As described in Example I, the presence of ASCA can be used to diagnose a medically resistant clinical subtype of UC. Moreover, the presence of the a2b1c2d4e1 haplotype also can be diagnostic of this subtype.

As further described in Example I, only one UC patient in the medically resistant group was both ASCA-positive and TNF haplotype a2b1c2d4e1-positive. Thus, the ASCA and a2b1c2d4e1 markers each can independently identify medically resistant UC patients. Accordingly, the present invention provides combined methods of diagnosing a clinical subtype of UC by determining both the presence or absence of ASCA and the presence or absence of the a2b1c2d4e1 haplotype, where either marker alone is indicative of the medically resistant UC subtype.

The present invention also provides combined serological methods of diagnosing a medically resistant clinical subtype of UC. The invention provides a method of diagnosing a medically resistant clinical subtype of UC by determining the presence or absence of a TNFa2b1c2d4e1 haplotype in a patient with UC and determining the presence or absence of ASCA in the patient with UC, where the presence of the TNFa2b1c2d4e1 haplotype indicates the medically resistant clinical subtype of UC and the presence of the ASCA independently indicates the medically resistant clinical subtype of UC.

The invention provides, for example, a method of diagnosing a medically resistant clinical subtype of UC where the presence or absence of ASCA is determined by obtaining a sample from the patient with UC, contacting the sample with antigen specific for ASCA under conditions suitable to form a complex of the antigen specific for ASCA and antibody to the antigen, and detecting the presence or absence of the complex, where the presence of the complex indicates that the patient has the medically resistant clinical subtype of UC.

The antigen specific for ASCA can be, for example, yeast cell wall phosphopeptidomannan (PPM) such as *S. cerevisiae* PPM and the presence or absence or the complex can be detected with one or more secondary antibodies having specificity for a class determining portion of the antibody to the antigen specific for ASCA.

As described herein, the presence of ASCA or the presence of the TNFa2b1c2d4e1 haplotype each is independently diagnostic of a medically resistant subtype of UC. The term "independently," when used herein in reference to the presence of a genetic or serological marker useful in a method of the invention, means that the genetic or serological marker, alone, is diagnostic of the medically resistant subtype of UC.

The invention also provides kits for diagnosing a medically resistant clinical subtype of ulcerative colitis containing antigen specific for ASCA and one or more oligonucleotide primers complementary to a nucleotide sequence flanking TNF microsatellite locus TNFa, TNFb, TNFc, TNFd or TNFe.

As described above, the term oligonucleotide primer complementary to a nucleotide sequence flanking a TNF locus means a linear oligonucleotide of about ten to about fifty nucleotides in length that is complementary to a nucleotide sequence 5' or 3' of a TNF locus or loci to be amplified. Such an oligonucleotide primer can have a nucleotide sequence including, for example, the nucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10. In the kits of the invention, an oligonucleotide primer can have, for example, the nucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10.

In the kits of the invention, the antigen specific for ASCA can be, for example, yeast cell wall phosphopeptidomannan (PPM) such as PPM extracted by autoclaving. The yeast cell wall PPM can be *S. uvarum* PPM and can be prepared, for example, from strain ATCC #38926. If desired, a kit for diagnosing a medically resistant clinical subtype of UC also can include one or more secondary antibodies selective for ASCA.

The following examples are intended to illustrate but not limit the present invention.

EXAMPLE I

Serum and Genetic Markers Define a Medically Resistant Clinical Subtype of Ulcerative Colitis This example demonstrates that the presence of ASCA and the presence of the TNF microsatellite haplotype a2b1c2d4e1 are significantly more frequent in patients with medically resistant UC than in patients with medically responsive UC.

Comprehensive clinical data was abstracted from 118 CD patients and 138 UC patients evaluated at our center. Diagnoses of CD and UC were established by standard criteria. The presence of TNF microsatellite haplotypes and the anti-*Saccharomyces cerevisiae* antibody marker (ASCA) were determined as described below. Clinical data were obtained without knowledge of the presence or absence of ASCA or the a2b1c2d4e1 haplotype. Similarly, the antibody and microsatellite markers were studied blinded to diagnosis and clinical profiles.

A group of clinically defined UC patients was evaluated for the presence of ASCA. In patients undergoing colectomy for medically resistant disease unresponsive to steroids, 5-aminosalicylic acid (5-ASA), 6-mercaptopurine (6-MP) and cyclosporin A, 19% were ASCA-positive as compared with only 2.9% ASCA positive of patients with medically responsive disease (p=0.04; see Table 6). These results indicate that the presence of ASCA is diagnostic of a medically resistant subtype of UC in a patient having UC.

A larger group of patients was examined for the presence of the a2b1c2d4e1 haplotype. This haplotype was present in 24.4% of CD patients, 13.5% of UC patients and 7.5% of non-inflammatory disease controls and was not over represented in subgroups of CD patients stratified for clinical parameters including response to medications, number of surgeries, fistulizing disease, fibrostenotic disease and disease location.

Ulcerative colitis patients also were stratified according to clinical parameters. The TNFa2b1c2d4e1 haplotype was present in 32% of patients with medically resistant UC unresponsive to steroids (100%), 5-ASA (100%), 6-MP (47%) or cyclosporin A (50%) who required colectomy as compared to 8.7% of patients who medically responded to steroids, 5-ASA or 6-MP (p=0.001). These results, which are summarized in Table 6, indicate that the presence of the TNFa2b1c2d4e1 haplotype is diagnostic of a medically resistant clinical subtype of UC in a patient with UC.

Only one UC patient in the medically resistant group was both ASCA-positive and a2b1c2d4e1 -positive. These results demonstrate that each of these markers (a2b1c2d4e1 haplotype and ASCA) can independently identify a subgroup of medically resistant UC patients.

TABLE 6

Frequency of ASCA and the TNF haplotype a2b1c2d4e1 in medically resistant and medically responsive UC

| Marker | Medically resistant UC | Medically responsive UC |
|---|---|---|
| ASCA-positive | 19% (6/31) | 2.9% (1/35) |
| a2b1c2d4e1-positive | 32% (11/34) | 8.7% (10/104) |

EXAMPLE II

ASCA ELISA Assay

This example demonstrates that the presence of anti-*Saccharomyces cerevisiae* antibodies in patient sera can be determined using an ELISA microplate assay.

Preparation of Yeast Cell Wall Mannan

Yeast cell wall mannan was prepared as follows and as described in Faille et al. *Eur. J. Clin. Microbiol. Infect. Dis.* 11:438–446 (1992) and in Kocourek and Ballou et al., *J. Bacteriol* 100:1175–1181 (1969), each of which is incorporated herein by reference. A lyophilized pellet of yeast *Saccharomyces uvarum* was obtained from the American Type Culture Collection (#38926). Yeast were reconstituted in 10 ml 2× YT medium, prepared according to Sambrook et al., *Molecular Cloning* Cold Spring Harbor Laboratory Press (1989), which is incorporated herein by reference. *S. uvarum* were grown for two to three days at 30° C. The terminal *S. uvarum* culture was inoculated on a 2× YT agar plate and subsequently grown for two to three days at 30° C. A single colony was used to inoculate 500 ml 2× YT media, and grown for two to three days at 30° C. Fermentation media (pH 4.5) was prepared by adding 20 gm glucose, 2 gm bacto-yeast extract, 0.25 gm $MgSO_4$ and 2.0 ml 28% $H_3PO_4$ per liter distilled water. The 500 ml culture was used to inoculate 50 liters of fermentation media, and the culture fermented for three to four days at 37° C.

*S. uvarum* mannan extract was prepared by adding 50 ml 0.02 M citrate buffer (5.88 gm/1 sodium citrate; pH 7.0±0.1) to each 100 grams of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolved in 6–8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded; then the wash procedure was repeated until the supernatant was colorless, approximately two to three times. The precipitate was collected on a scintered glass funnel, washed with methanol and air dried overnight. On some occasions, the precipitate was collected by centrifugation at 5000 rpm for 10 minutes before washing with methanol and air drying overnight. The dried mannan powder was dissolved in distilled waster, using approximately 5 ml water per gram of dry mannan powder. The final concentration of S. uvarum cell wall mannan was approximately 30 μg/ml.

Preparation of S. uvarum Mannan ELISA Plates

S. uvarum cell mannan ELISA plates were saturated with antigen as follows. Purified S. uvarum mannan prepared as described above was diluted to a concentration of 100 μg/ml with phosphate buffered saline/0.2% sodium azide (PBS-N3). Using a multi-channel pipettor, 100 μl of 100 μg/ml S. uvarum mannan was added per well of a Costar 96-well hi-binding plate (catalogue number 3590; Costar Corp., Cambridge, Mass.). The antigen was allowed to coat the plate at 4° C. for a minimum of 12 hours. Each lot of plates was compared to a previous lot before use. Plates were stored at 2–8° C. for up to one month.

Analysis of Patient Sera

Patient sera were analyzed in duplicate for anti-IgG or anti-IgA reactivity. Microtiter plates saturated with antigen as described above were incubated with phosphate buffered saline/0.05% Tween-20 for 45 minutes at room temperature to inhibit nonspecific antibody binding. Patient sera were subsequently added at a dilution of 1:800 for IgG and 1:80 for IgA and incubated for 1 hour at room temperature. Wells were washed three times with PBS/0.05% Tween-20. Then a 1:1000 dilution of alkaline phosphatase-conjugated goat anti-human IgG F(Ab)$_2$ (Pierce, Rockford, Ill.) or a 1:1000 dilution of alkaline phosphatase-conjugated goat anti-human IgA (Jackson Immunoresearch, Westgrove, Pa.) was added, and the microtiter plates incubated for 1 hour at room temperature. A solution of p-nitrophenol phosphate in diethanolamine substrate buffer was added, and color development allowed to proceed for 10 minutes. Absorbance at 405 nm was analyzed using an automated EMAX plate reader (Molecular Devices, Sunnyvale, Calif.).

Standard binding of pooled sera from patients with an established diagnosis of Crohn's disease was used as a standard reference for binding and set to be 100 ELISA units. Results with test patient sera were expressed as a percentage of the standard binding of the reference CD sera. ASCA-positivity was defined as anti-IgG ASCA reactivity that was greater than 40% of the reference CD sera or anti-IgA ASCA reactivity that was greater than 20% of the reference CD sera. Using these criteria, samples that were positive with only anti-IgG or only anti-IgA were considered to be ASCA-positive.

EXAMPLE III

Preparation of Purified Antigen Specific for ASCA

This example demonstrates that an oligomannoside can be released from yeast cell wall phosphopeptidomannan and used to produce a neoglycolipid antigen specific for ASCA.

Neoglycolipid antigen specific for ASCA is prepared as follows. Briefly, PPM from an appropriate yeast strain is acetolyzed essentially by the method of Hamada et al., *Applied and Environmental Microbiology*, 48:708–712 (1984). The PPM is dissolved in 10 ml of formamide, mixed with 50 ml of acetic anhydride-pyridine (vol/vol), and heated for 13 hours at 30° C. on a rotary shaker. This solution is then poured into water and centrifuged at 1,500×g for 15 minutes. The pellet is dried, suspended in 50 ml of acetic anhydride-acetic acid (100:100:1), and heated for 13 hours at 40° C. on a rotary shaker. The reaction is stopped by pouring the solution onto ice, and the mixture is neutralized with sodium bicarbonate. The released oligosaccharides are extracted with chloroform, incubated for 15 minutes at room temperature in 10 ml of methanol (adjusted to pH 9 with sodium methoxide), and centrifuged for 15 min at 1,500×g. The pellet is then washed twice in methanol and dissolved in water. The released oligomannosides are separated on a BioGel P2 column (Bio-Rad, Hercules, Calif.; 1.0 by 120 cm). The column is eluted with distilled water at a flow rate of 4 ml/hour at room temperature; approximately 0.6 ml fractions are collected and coupled to 4-hexadecylanaline as described in Faille et al., *Infection and Immunity*, 58:3537–3544 (1990), which is incorporated herein by reference.

Neoglycolipids are constructed from oligomannosides released from the cell wall PPM as described above. PPM is depleted in oligosaccharides released after mild acid hydrolysis(oligomannosides linked by phosphodiester bridges) and in oligosaccharides released after β-elimination (oligomannosides linked by O-glycoside bonds to the peptide moiety). This depleted PPM is subsequently acetylated and acetolysed in order to release the polysaccharide side chains according to the method described by Hamada et al., *Applied and Environmental Microbiology*, 48:708–712 (1984); the acetolysis solution is composed of acetic anhydride:acetic acid:sulfuric acid (20:20:1, vol/vol/vol).

The procedure for construction of neoantigens from these oligomannosides is adapted from that described by Tang et al., *Biophysical Research Communications*, 132:474–480 (1985), as previously described (Faille et al., supra, 1990, with slight modifications). Briefly, 100 mg 4-hexadecylaniline (Aldrich Chemical, U.S.A.) is added to 500 μl of a solution containing 35 mg sodium cyanoborohydride, 3.5 ml methanol and 400 μl acetic acid. The solution is heated, and 2 mg of oligosaccharides solubilized in 20 μl of water are added. After 90 min at 80° C., the solution is cooled, mixed with 2 ml of chloroform and water (1:1, vol/vol) and centrifuged. The lower phase is discarded. The upper phase is washed again with chloroform (1 ml), dried, dissolved in methanol (2 ml), and centrifuged. The pellet, containing the uncoupled oligosaccharides is discarded.

EXAMPLE IV

PCR Analysis of TNF Microsatellite Alleles

This example demonstrates that PCR analysis can be used to distinguish alleles at the TNFa, TNFb, TNFc, TNFd and TNFe loci based on size. Oligonucleotides used as PCR primers for TNF microsatellite analysis, shown in Table 7, were synthesized at the Cedars-Sinai Medical Center core DNA synthesis facility from sequences published in Udalova et al., supra, 1993. Genomic DNA from patients and controls was amplified using a two-step PCR procedure as follows. The first PCR was performed with primers SEQ ID NO:1 and SEQ ID NO:2 (for TNFa and TNFb), SEQ ID NO:7 and SEQ ID NO: 10 (for TNFd and TNFe), and SEQ ID NO:5 and SEQ ID NO:6 (for TNFc). Primer pairs at a final concentration of0.15 μmol/L each were added in a total reaction volume of 20 μL with 10 mmol/L Tris-HCl (pH 8.3); 50 mmol/L KCl; 2 mmol/L MgCl$_2$; 200 μmol/L each deoxyadenosine triphosphate, deoxyguanosine triphosphate, deoxycytidine triphosphate, and deoxyribosylthymine triphosphate; 100–500 ng genomic DNA; and 1U Amplitaq DNA polymerase (Perkin-Elmer Cetus, Norwalk, Conn.) PCR was performed in a 480 thermal cycler (Perkin-Elmer Cetus) under the following conditions: 94° C. for 7 minutes and then 25 cycles at 94° C. for 60 seconds, 60° C. for 60 seconds, and 72' for 60 seconds followed by a 5-minute extension at 72° C.

During the second PCR, DNA fragments at each TNF microsatellite loci were amplified separately. Two microliters of the first PCR reaction was added to reagents in the same final concentrations as in the first PCR to a total volume of 20 μl. For TNFa and TNFb typing, concentrations were the same as in the first PCR in a total volume of 20 μl. For TNFa, primer SEQ ID NO: 3 was added, and for TNFb typing, primer SEQ ID NO:4 was added. For TNFd typing, primer SEQ ID NO: 8 was added to the SEQ ID NO:7 and SEQ ID NO: 10 reaction. For TNFe typing, primer SEQ ID NO: 9 was added to the SEQ ID NO:7 and SEQ ID NO: 10 reaction. For TNFc, primers SEQ ID NO:5 and SEQ ID NO:6 were readded to a final concentration of 0.15 μmol/L. Deoxyguanosine triphosphate, deoxycytidine triphosphate, and deoxyribosylthymine triphosphate were added to the same final concentration as in the first PCR reaction. Deoxyadenosine triphosphate were replaced with 5 μCi 35S-α-deoxyadenosine triphosphate in the second PCR. After 7 minutes at 94° C., 6 cycles of PCR were completed at the same times and temperatures as the first PCR, followed by a 5-minute extension at 72° C.

After the second round of amplification, 3 μl of each sample was denatured by boiling and electrophoresed on a 7 mol/1 urea, 6% polyacrylamide, 0.4-mm sequencing gel at 1500 V. Gels were run with a 35S-β-deoxyadenosine triphosphate-labeled pGEM–3Zs (+) control DNA sequencing marker (Promega, Madison, Wis.) to size fragments. Two-step PCR was also performed with genomic DNA from CEPH/ASHI cell lines (provided by Pat Concannon and Dolly Tyan) previously typed at all 5 TNF microsatellite loci as controls. Internal standards were necessary for unambiguous allele interpretations, particularly at the TNFb and TNFd loci. PCR product from at least one standard cell line per TNF microsatellite locus was electrophoresed with the sample DNA. Gels were subsequently dried and autoradiographed with XAR-5 X-ray film (Kodak Corp., Rochester, N.Y.) and one intensifying screen at −70° C. for 48 to 72 hours. Microsatellite alleles differ by one dinucleotide repeat for TNFa, TNFc, TNFd, and TNFe. For TNFb, alleles differ by 1 or 2 bases as reported in Udalova et al., supra, 1993). For each of the TNF microsatellite alleles, the smallest allele is termed 1 with larger alleles numbered consecutively.

TABLE 7

Oligonucleotide Primer Sequences for Amplification of TNF Microsatellite loci

| TNF loci | SEQ ID NO: | Primer sequence |
|---|---|---|
| a and b | SEQ ID NO: 1<br>SEQ ID NO: 2 | 5'-GCACTCCAGCCTAGGCCACAGA-3'<br>5'-GCCTCTAGATTTCATCCAGCCACA-3' |
| a only | SEQ ID NO: 2<br>SEQ ID NO: 3 | 5'-GCCTCTAGATTTCATCCAGCCACA-3'<br>5'-CCTCTCTCCCCTGCAACACACA-3' |
| b only | SEQ ID NO: 1<br>SEQ ID NO: 4 | 5'-GCACTCCAGCCTAGGCCACAGA-3'<br>5'-GTGTGTGTTGCAGGGGAGAGAG-3' |
| c only | SEQ ID NO: 5<br>SEQ ID NO: 6 | 5'-GGTTTCTCTGACTGCATCTTGTCC-3'<br>5'-TCATGGGGAGAACCTGCAGAGAA-3' |
| d and e | SEQ ID NO: 7<br>SEQ ID NO: 10 | 5'-AGATCCTTCCCTGTGAGTTCTGCT-3'<br>5'-TGAGACAGAGGATAGGAGAGACAG-3' |
| d only | SEQ ID NO: 7<br>SEQ ID NO: 8 | 5'-AGATCCTTCCCTGTGAGTTCTGCT-3'<br>5'-CATAGTGGGACTCTGTCTCCAAAG-3' |
| e only | SEQ ID NO: 9<br>SEQ ID NO: 10 | 5'-GTGCCTGGTTCTGGAGCCTCTC-3'<br>5'-TGAGACAGAGGATAGGAGAGACAG-3' |

All journal article, reference and patent citations provided above, in parentheses or otherwise, whether previously stated or not, are incorporated herein by reference in their entirety.

Although the invention has been described with reference to the examples above, it should be understood that various modifications can be made without departing from the spirit of the invention. Accordingly, the invention is limited only by the following claims.

We claim:

1. A method of diagnosing a medically resistant clinical subtype of ulcerative colitis (UC), comprising determining the presence or absence of anti-*Saccharomyces cerevisiae* antibodies (ASCA) in a patient with UC, wherein the presence of said ASCA indicates said medically resistant clinical subtype of UC.

2. The method of claim 1, wherein the presence of ASCA is determined by an immunoassay.

3. The method of claim 1, wherein determining the presence or absence of said ASCA comprises the steps of:

(a) obtaining a sample from said patient with UC;

(b) contacting said sample with antigen specific for ASCA, under conditions suitable to form a complex of said antigen specific for ASCA and antibody to said antigen; and (c) detecting the presence or absence of said complex, wherein the presence of said complex indicates said medically resistant clinical subtype of UC.

4. The method of claim 3, wherein said antigen is yeast cell wall phosphopeptidomannan (PPM).

5. The method of claim 4, wherein said yeast cell wall PPM is extracted by autoclaving.

6. The method of claim 4, wherein said yeast cell wall PPM is acid stable.

7. The method of claim 4, wherein said yeast cell wall PPM is *S. cerevisiae* PPM.

8. The method of claim 4, wherein said yeast cell wall PPM is prepared from the strain having ATCC #38926.

9. The method of claim 3, wherein said antigen specific for ASCA comprises mannotetraose Man(1→3)Man(1→2)Man(1→2)Man.

10. The method of claim 3, wherein said antigen specific for ASCA is whole killed yeast.

11. The method of claim 10, wherein said whole killed yeast is whole killed *S. cerevisiae*.

12. The method of claim 10, wherein said whole killed yeast is a strain having ATCC #38926.

13. The method of claim 3, wherein the presence or absence of said complex is detected with one or more secondary antibodies, wherein said one or more secondary antibodies have specificity for a class determining portion of said antibody to said antigen specific for ASCA.

14. The method of claim 13, wherein said one or more secondary antibodies is anti-immunoglobulin A.

15. The method of claim 13, wherein said one or more secondary antibodies is anti-immunoglobulin G.

16. The method of claim 13, wherein said one or more secondary antibodies are anti-immunoglobulin A and anti-immunoglobulin G.

17. The method of claim 13, wherein said one or more secondary antibodies are detectable secondary antibodies.

18. A method of diagnosing a medically resistant clinical subtype of UC, comprising determining the presence or absence of at least two TNF microsatellite alleles selected from the group consisting of TNFa2, TNFb1, TNFc2, TNFd4 and TNFe1 in a patient with UC, wherein the presence of an allelic combination comprising at least two of said alleles indicates a medically resistant clinical subtype of UC.

19. The method of claim 18, comprising detecting at least three of said alleles selected from the group consisting of TNFa2, TNFb1, TNFc2, TNFd4 and TNFe1 in said patient with UC, wherein the presence of an allelic combination comprising at least three of said alleles indicates a medically resistant subtype of UC.

20. The method of claim 19, wherein said allelic combination comprises TNF microsatellite alleles TNFa2, TNFb1 and TNFc2.

21. The method of claim 19, wherein said allelic combination comprises TNF microsatellite alleles TNFa2, TNFb1, TNFc2 and TNFd4.

22. The method of claim 19, wherein said allelic combination comprises TNF microsatellite alleles TNFa2, TNFb1, TNFc2 and TNFe1.

23. A method of diagnosing a medically resistant clinical subtype of UC, comprising determining the presence or absence of a TNFa2b1c2d4e1 haplotype in a patient with UC, wherein the presence of said TNFa2b1c2d4e1 haplotype indicates said medically resistant clinical subtype of UC.

24. The method of claim 23, wherein determining the presence or absence of a TNFa2b1c2d4e1 haplotype comprises the steps of:
  (a) obtaining material comprising nucleic acid including TNFa, TNFb, TNFc, TNFd and TNFe loci from said patient;
  (b) enzymatically amplifying said nucleic acid using pairs of oligonucleotide primers complementary to nucleotide sequences flanking each of said TNFa, TNFb, TNFc, TNFd and TNFe loci to produce amplified products including TNFa, TNFb, TNFc, TNFd or TNFe; and
  (c) electrophoresing said amplified products to identify said TNFa2b1c2d4e1 haplotype.

25. The method of claim 24, wherein one or more of said oligonucleotide primers is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

26. The method of claim 24, wherein a first pair of oligonucleotide primers SEQ ID NO: 2 and SEQ ID NO: 3 produce amplified product including locus TNFa,
  a second pair of oligonucleotide primers SEQ ID NO: 1 and SEQ ID NO: 4 produce amplified product including locus TNFb,
  a third pair of oligonucleotide primers SEQ ID NO: 5 and SEQ ID NO: 6 produce amplified product including locus TNFc,
  a fourth pair of oligonucleotide primers SEQ ID NO: 7 and SEQ ID NO: 8 produce amplified product including locus TNFd and
  a fifth pair of oligonucleotide primers SEQ ID NO: 9 and SEQ ID NO: 10 produce amplified product including locus TNFe.

27. The method of claim 23, wherein determining the presence or absence of a TNFa2b1c2d4e1 haplotype comprises:
  (a) obtaining material comprising nucleic acid including TNFa, TNFb, TNFc, TNFd and TNFe loci from said patient;
  (b) enzymatically amplifying said nucleic acid using pairs of oligonucleotide primers complementary to nucleotide sequences flanking each of said TNFa, TNFb, TNFc, TNFd and TNFe loci to produce amplified products including TNFa, TNFb, TNFc, TNFd or TNFe; and
  (c) sequencing said amplified products to identify said TNFa2b1c2d4e1 haplotype.

28. A method of diagnosing a medically resistant clinical subtype of UC, comprising the steps of:
  (a) determining the presence or absence of a TNFa2b1c2d4e1 haplotype in a patient with UC and
  (b) determining the presence or absence of ASCA in said patient with UC,
  wherein the presence of said TNFa2b1c2d4e1 haplotype indicates said medically resistant clinical subtype of UC and
  the presence of said ASCA independently indicates said medically resistant clinical subtype of UC.

29. The method of claim 28, wherein determining the presence or absence of ASCA further comprises:
  (b1) obtaining a sample from said patient with UC;
  (b2) contacting said sample with antigen specific for ASCA, under conditions suitable to form a complex of said antigen specific for ASCA and antibody to said antigen; and
  (b3) detecting the presence or absence of said complex, wherein the presence of said complex indicates that said patient has said medically resistant clinical subtype of UC.

30. The method of claim 29, wherein said antigen is yeast cell wall phosphopeptidomannan (PPM).

31. The method of claim 29, wherein said yeast cell wall PPM is S. cerevisiae PPM.

32. The method of claim 29, wherein said yeast cell wall PPM is prepared from strain ATCC #38926.

33. The method of claim 29, wherein the presence or absence of said complex is detected with one or more secondary antibodies, wherein said one or more secondary antibodies have specificity for a class determining portion of said antibody to said antigen specific for ASCA.

34. The method of claim 33, wherein said one or more secondary antibodies is anti-immunoglobulin A.

35. The method of claim 33, wherein said one or more secondary antibodies is anti-immunoglobulin G.

36. The method of claim 33, wherein said one or more secondary antibodies are anti-immunoglobulin A and anti-immunoglobulin G.

37. A kit for diagnosing a medically resistant clinical subtype of UC, comprising antigen specific for ASCA and one or more oligonucleotide primers complementary to a nucleotide sequence flanking a TNF microsatellite locus selected from the group consisting of TNFa, TNFb, TNFc, TNFd and TNFe.

38. The kit of claim 37, wherein said oligonucleotide primer comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

39. The kit of claim 37, wherein said oligonucleotide primer consists of a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

40. The kit of claim 37, wherein said antigen is yeast cell wall PPM.

41. The kit of claim 40, wherein said yeast cell wall PPM is extracted by autoclaving.

42. The kit of claim 40, wherein said yeast cell wall PPM is S. cerevisiae PPM.

43. The kit of claim 40, wherein said yeast cell wall PPM is prepared from strain ATCC #38926.

44. The kit of claim 37, further comprising one or more secondary antibodies selective for ASCA.

45. The kit of claim 44, wherein said one or more secondary antibodies selective for ASCA is anti-IgA.

46. The kit of claim 44, wherein said one or more secondary antibodies selective for ASCA are anti-IgG and anti-IgA.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear    (xi) SEQUENCE DESCRIPTION: SEQ ID NO:1:

GCACTCCAGC CTAGGCCACA GA                                        22

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single (D) TOPOLOGY: linear (xi) SEQUENCE DESCRIPTION: SEQ ID NO:2:

GCCTCTAGAT TTCATCCAGC CACA                                            24

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:3:

CCTCTCTCCC CTGCAACACA CA                                              22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

GTGTGTGTTG CAGGGGAGAG AG                                              22

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

GGTTTCTCTG ACTGCATCTT GTCC                                            24

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

TCATGGGGAG AACCTGCAGA GAA                                             23

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

AGATCCTTCC CTGTGAGTTC TGCT                                            24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
        (xi) SEQUENCE DESCRIPTION: SEQ ID NO:8:

CATAGTGGGA CTCTGTCTCC AAAG                                              24

(2) INFORMATION FOR SEQ ID NO:9:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (xi) SEQUENCE DESCRIPTION: SEQ ID NO:9:

GTGCCTGGTT CTGGAGCCTC TC                                                22

(2) INFORMATION FOR SEQ ID NO:10:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (xi) SEQUENCE DESCRIPTION: SEQ ID NO:10:

TGAGACAGAG GATAGGAGAG ACAG                                              24
```